United States Patent [19]

Herbold

[11] 4,419,989

[45] Dec. 13, 1983

[54] TILTABLE RECLINING AND SEATING DEVICE

[76] Inventor: Ted E. Herbold, 1909 E. 28th Ave., North Kansas City, Mo. 64116

[21] Appl. No.: 251,184

[22] Filed: Apr. 6, 1981

[51] Int. Cl.[3] ................................................ A61F 5/00

[52] U.S. Cl. ........................................ 128/74; 272/145

[58] Field of Search .................... 254/122; 128/72–75; 272/144–145; 108/6, 7, 8

[56] References Cited

U.S. PATENT DOCUMENTS

| | | | |
|---|---|---|---|
| 1,453,013 | 4/1923 | Koenigkramer | 128/74 |
| 2,002,349 | 5/1935 | Lundeen | 128/72 |
| 2,451,607 | 10/1948 | Binash | 128/72 |
| 3,160,228 | 12/1964 | Steed | 254/122 |
| 3,210,779 | 10/1965 | Herbold | 128/74 |
| 4,142,520 | 3/1979 | Herbold | 128/74 |

*Primary Examiner*—Richard J. Apley
*Assistant Examiner*—David J. Brown
*Attorney, Agent, or Firm*—Thomas M. Scofield

[57] ABSTRACT

Improvements in mechanisms and devices for reclining the recumbent human body in an inclined, head-downward position from an initial horizontal position and returning it to such horizontal position; improvements in user hand operated drive mechanisms wherein the reclined user of the device may readily affectuate and control both the rate and degree of recline and return in such devices; stabilizing mechanisms and constructions for smoothly, uniformly and dependably inclining and returning a seated or recumbent reclining device; improvements in reclining devices for use in seated or recumbent positions of the operator/user.

13 Claims, 19 Drawing Figures

60
68
68a
63b
63
62
70
64
69
69a
64b
20b
61
7.
8.
57d
64a
66
57a
57c
57b
63a
67
57
59
49a
43'
49
49b
58a
65

TILTABLE RECLINING AND SEATING DEVICE

BACKGROUND OF THE INVENTION

It is believed to be well established that periodically subjecting the normal individual human body to a recumbent, head downwards position, for limited periods of time, has beneficial and important health effects. Numerous frames, machines and devices have been developed over the years for achieving this function and body position. A number of these particular devices are recorded herebelow in the listing of the prior art. The immediately following remarks are intended to give a rationale to the operation of the subject device, in addition to those beneficial effects, premises and goals heretofore delineated in the literature. The rationales and benefits of the noted prior art will not here be repeated, but are herein incorporated by reference. With respect to the latter, applicant is specifically referring to those physiological and health effects and benefits which are believed to result from a reclined, head downward position of the supine human body, with the weight of the body preferably being suspended from the feet or ankles of the individual.

A reverse gravity theory may be postulated to the effect that men are victims of a natural, inherent handicap causing accelerated physical deterioration that may or should not be wholly attributed to longevitity and aging. Specifically, man's vertical posture, as effected by the pull of gravity (and increased in many cases by obesity) eventually creates a pinching and choking effect both on the nerves and blood vessels, particularly at those points where they emerge through the openings between the vertebrae and the spinal column. Such a theory is supported not only by anatomical and physiological evidence, but also by plausible supposition.

Thus, the length of the spinal column, in the average adult male, at about the age of 30, is substantially 28 inches. Such is curved and flexible and held together by muscles and ligaments. Separating each of the 26 adjacent vertebrae is an intervertebral disc, made up of tough, fibrous cartilage. The total thickness of all of these discs, placed one on top of the other, is approximately 5 inches.

Through a vertical hole (spinal foramen) in each vertebra runs the spinal cord, which extends from the lower brain and skull down to the coccyx. This cord consists of 31 pairs of nerve segments bound together like a cable. The 31 pairs of nerve segments, excepting the first cervical nerve pair, emerge outwardly through the openings between each vertebra and continue, through muscles and ligaments, to the various parts of the body, thus giving 30 nerve segments on each side of the spine. The main openings are supported by the intervertebral discs discussed above. Also through each of these same openings passes a vein and an artery to supply the spinal cord with its necessary blood supply. The emerging nerves of voluntary and involuntary reaction branch out to supply the skin, bodily organs and glands their life functioning impetus.

Statistics of the U.S. Department of Health, Education and Welfare show that the average man shrinks in height over three inches between the ages of 30 and 79. This shrinkage mostly occurs with respect to the intervertebral discs, since the bones themselves do not shrink. Thus, apparently, three inches of shrinking occur in what was originally about five inches of cartilage, thus a shrinkage of over 50%. The subject theory postulates that, as this shrinkage occurs over time, a pinching effect emerges and develops on the nerves and blood vessels at points where they emerge from the spinal cord. Such would naturally hamper their functional ability, resulting in slow physical deterioration of the muscles, glands and organs they serve.

It is a further postulate of the reverse gravity theory, that, if the spinal column is periodically depressurized, by inverting the bodily position, with, as a result, relief of the described pinching under controlled stretch treatments, the particular nerve and blood vessels will have a chance to restore themselves and react as they should. At the same time, the blood supply will be increased in the upper extremities and the head.

The subject device is directed to achieving the described effects in the most efficient, safe and beneficial manner. The degree of bodily incline can be regulated as desired between horizontal and a maximum inclination which is far from the vertical, yet sufficiently achieves the desired effects within a reasonable time. This stretching of the elements of the body with respect to one another is provided by the pull of the body weight alone, that is, no traction is employed. The effort involved requires no more than five to ten minutes a day, preferably just before retiring. Thus, if one goes to bed after use of the device, the spine does not quickly rebound to its former tight position as the body, in a horizontal position, tends to nullify the gravity pull until the next morning, at least.

The particular goal of the subject improvement is to provide an optimum device whereby, through a series of such treatments, hopefully, the youthful process is prolonged or restored, the aging process is relatively arrested and a general improvement in bodily appearance, muscle tone and general well being may be noticed and achieved.

THE PRIOR ART

Basically, the subject improvements comprise developments of and over the structures of the devices of my two patents, specifically, U.S. Pat. No. 3,210,779 "Multiple Position Combination Chair Bed", issued Oct. 12, 1965 and U.S. Pat. No. 4,142,520, issued Mar. 6, 1979, for "Tiltable Reclining And Seating Device". In addition to these patents, applicant is aware of other related prior art which, basically, divides into the following categories:

The first of these are patents relating to beds (typically hospital beds) adaptable to movement of a patient supporting frame into Trendelenburg and reversed Trendelenburg positions. Examples of these types of devices are seen in the following patents:

Turko et al U.S. Pat. No. 3,611,452, issued Oct. 12, 1971, "Invalid Bed Construction";

Szucs, U.S. Pat. No. 3,678,509, issued July 25, 1972 for "Hospital Bed";

Kirkland U.S. Pat. No. 3,711,876, issued Jan. 23, 1973 for "Tilt Bed"; and

Saternus, U.S. Pat. No. 3,722,010, issued Mar. 27, 1973 for "Adjustable Hospital Bed".

A second class of devices, boards, couches, apparatus, tables or beds is directed to essentially the same goal as the subject device. Specifically, these devices are adapted to recline the recumbent human body into a tilted, head-downward position for various therapeutic healthful effects, such as noted above. The following patents exemplify this type of device:

Hoppe U.S Pat. No. 2,176,342, issued Oct. 17, 1939 for "Health Balancing Board";

Sprague U.S. Pat. No. 2,932,038, "Couch", issued Apr. 12, 1967;

De Girolamo U.S. Pat. No. 3,081,085 "Back Posture And Stretch Board", issued Mar. 12, 1963;

Heisler et al U.S. Pat. No. 3,152,802 "Therapeutic and Body Exercising Apparatus", issued Oct. 13, 1964;

Jennings U.S. Pat. No. 3,351,051 "Treatment Table With Rocking Means", issued Nov. 7, 1967;

Stites U.S. Pat. No. 3,568,689, issued Mar. 9, 1971 for "Tilting Health Table";

Kotter U.S. Pat. No. 3,579,671 "Adjustable Bed", issued May 25, 1971; and

Bolmberg U.S. Pat. No. 3,588,929 "Adjustable Tilting Device . . . ", issued June 29, 1971.

Next, there are devices, typically medical, for positioning patients at various reclining positions, including hospital beds, operating tables, hospital tables and the like. Exemplary of these are:

Hawk U.S. Pat. No. 1,529,699, issued Mar. 17, 1925 "Adjustable Hospital Bed";

Alopeaus U.S. Pat. No. 2,186,660 "Operating Table", issued Jan. 9, 1940;

Climo U.S. Pat. No. 2,763,520, issued Sept. 18, 1956 "Rollable and Tiltable Hospital Table";

Ohrberg U.S. Pat. No. 3,293,667, issued Dec. 27, 1966 "Adjustable . . . Tilting . . . Bed"; and U.S. Pat. No. 3,789,437 Garte, issued Feb. 5, 1974 for "Folding Hospital Bed".

Reference is also made to:

H. L. Thompson U.S. Pat. No. 2,267,054 "Chiropractic Table", issued Dec. 23, 1941 and Lorang U.S. Pat. No. 2,702,733 "Adjustable Head Rest For Chiropractic Tables", issued Feb. 22, 1955.

OBJECTS OF THE INVENTION

A first object of the invention is to substantially improve the devices of my two U.S. patents, specifically, U.S. Pat. No. 3,210,779 "Multiple Position Combination Chair Bed", issued Oct. 12, 1965 and U.S. Pat. No. 4,142,520, issued Mar. 6, 1979 for "Tiltable Reclining And Seating Device".

Another object of the invention is to substantially improve over those devices of the prior art which are directed to means for reclining the recumbent human body in a downwardly angled, head-down position for healthful therapeutic effects.

Another object of the invention is to provide an improved reclining frame for use in devices of the character described, where not only is the entire weight of the subject, user or operator suspended from the foot and ankle zone of the individual, but, additionally, a protective guard is provided at the head end of the device for limiting the downward inclinational movement of the body supporting frame, thereby to obviate any chance or opportunity for the head of the subject to contact or strike the floor or ground zone.

A further object of the invention is to provide improved structural and functional means for variably reclining (at lesser to greater degrees of incline, as desired) a normally horizontal, body receiving frame, so that said frame may be reclined at any desired angle from horizontal to the maximum angle of recline without slippage and with complete safety, the body receiving frame being (1) returnable toward the horizontal position or (2) reclinable to a greater angle, after reaching a given angle of recline.

Yet another object of the invention is to provide a simple, powerful, effective and safe drive system for a reclinable body-receiving frame which permits the recumbent user or operator (individual supine on the frame) to not only move the device from the horizontal to a partly or fully reclining position, but also return same readily to the horizontal position with a minimum of effort and discomfort.

A further object of the invention is to provide substantial improvements in the art of reclining chairs wherein the subject previously described frame may be translated to a stable chair position, the resulting chair also tiltable to the maximum degree (or any selected lesser degree) of the reclining body receiving frame and, further, returnable therefrom by simple, safe, handy, powerful, wheel operated means.

Another object of the invention is to provide new improvements in means and devices for converting a horizontal or flat body receiving frame to a chair back frame, and back, which means are a simple, dependable, strong and useable over and over again without deterioration in safety or efficiency.

Yet another object of the invention is to provide such a device of the character described which is (1) relatively simple in construction, (2) fabricated of a minimum number of parts, (3) rugged in long use, service and operation, (4) relatively cheap to manufacture and (5) which has a long life of use without requirement of excessive repair or replacement of the parts. Yet further, all of the parts of the device are readily accessible at all times for inspection, maintenance or repair, there being no structural or functional part which is not at all times readily visible.

Other and further objects of the subject invention will appear in the course of the following description thereof.

THE DRAWINGS

In the drawings, which form a part of the instant specification and are to be read in conjunction therewith, an embodiment of the invention as shown and, in the various views, like numerals are employed to indicate like parts.

FIG. 1, in full lines, shows a side elevation of subject device in horizontal or level position of the body receiving frame. The dotted line showing illustrates the elevation of the right hand side of the frame in the view to form the chair back and arm construction for the alternate use of the device as seen in FIG. 18.

4 and 5 to show the center deflections of these beam members.

Figures 4, 5, 6, 7, 8:
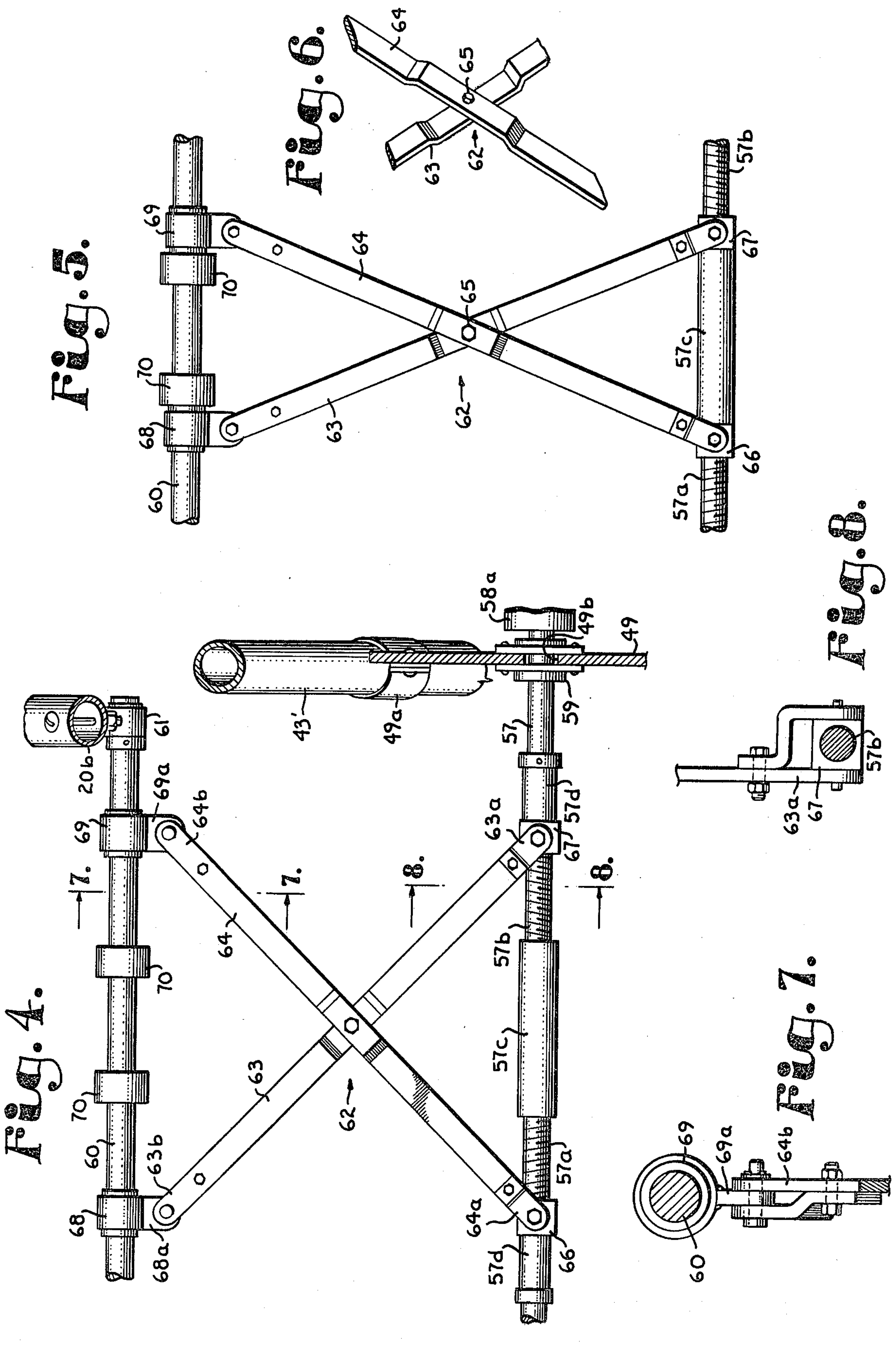
FIG. 4 is a view taken along the line 4—4 of FIG. 1 in the direction of the arrows.
FIG. 5 is a fragmentary view of the left center portion of the device of FIG. 4, but with the X form elevating and reclining means moved or translated to the position which results in the inclination or slope of FIG. 2 (or FIG. 18).
FIG. 6 is a fragmentary three-quarter perspective view from above of the center of the X frame of FIGS.

FIG. 7 is a view taken along the line 7—7 of FIG. 4 in the direction of the arrows.

FIG. 8 is a view taken along the line 8—8 of FIG. 4 in the direction of the arrows.

Figure 1:
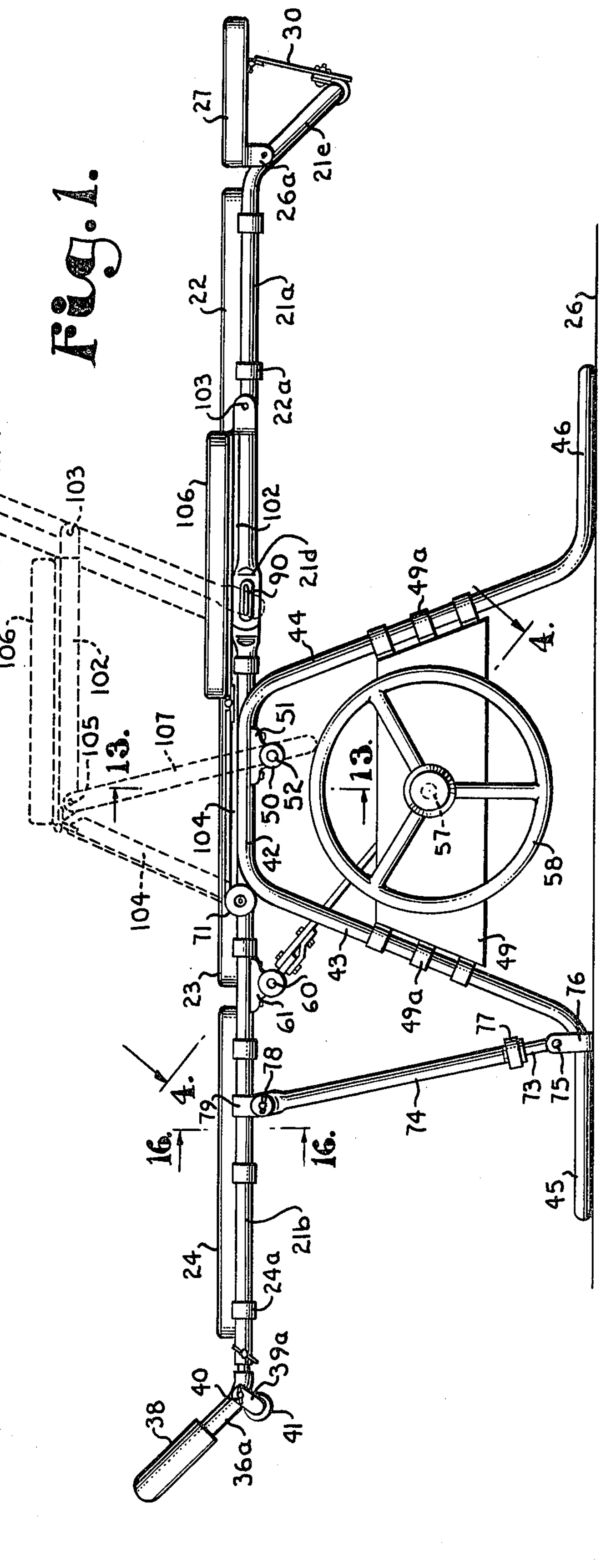
Figure 2:
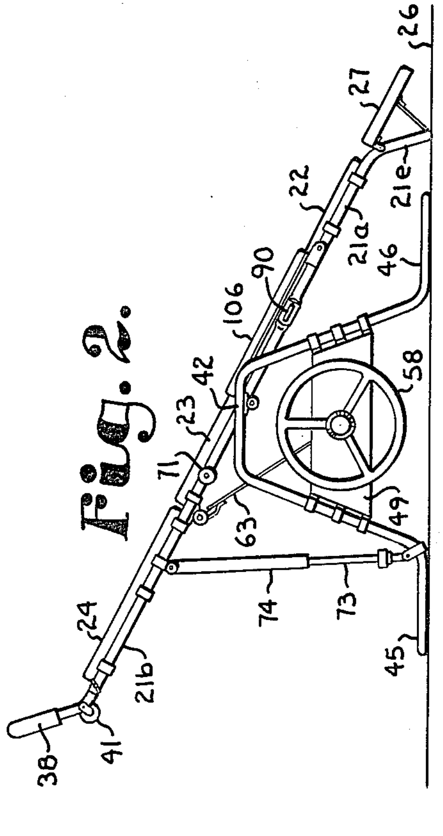
FIG. 2 is a view like the full line showing of FIG. 1, but with the body receiving frame of the device tilted or angled so that the foot end is up and the head end is down.
Figure 9:
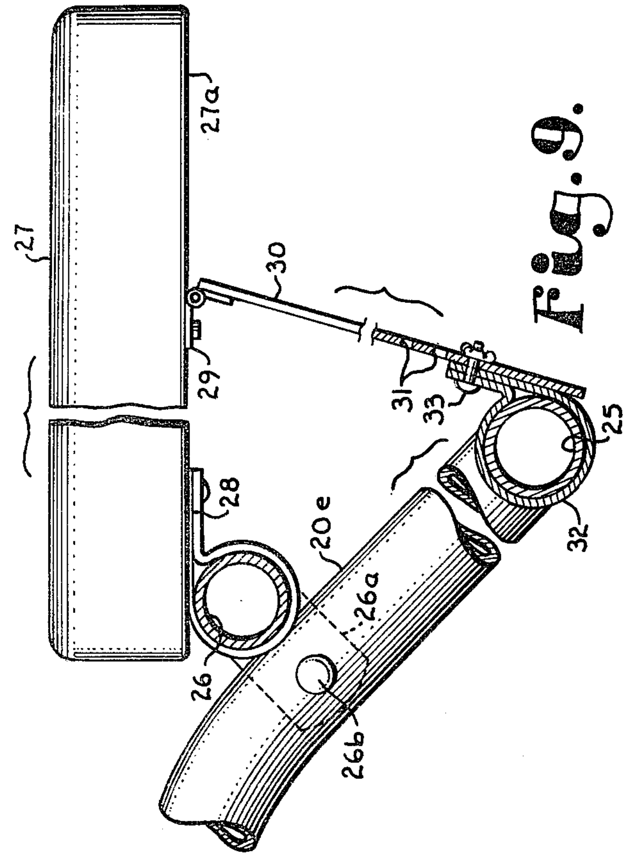

FIG. 9 is an enlarged, somewhat condensed detail of the right hand end of the frame of FIGS. 1 and 2 showing the adjustability of the head pad used in the sitting option. This is a view taken along the line 9—9 of FIG. 3 in the direction of the arrows.

Figure 10:
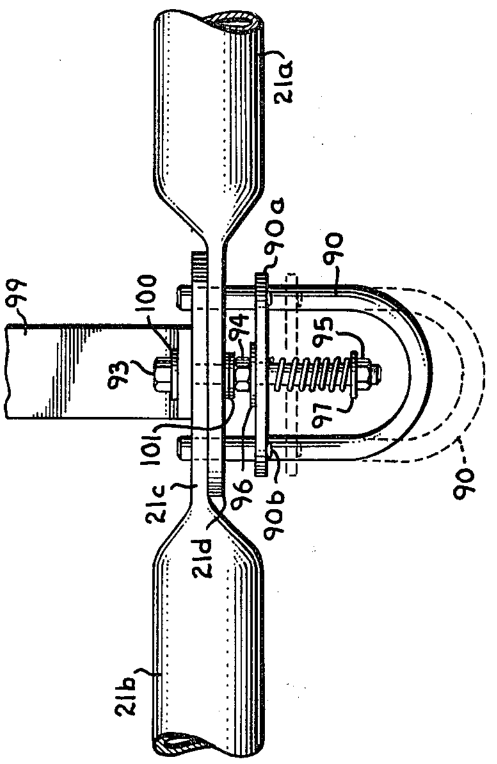
Figure 12:
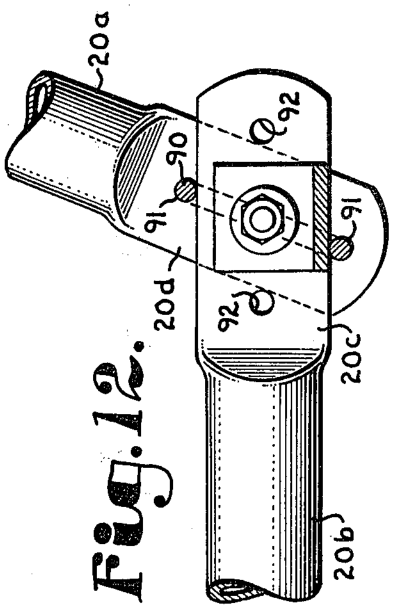
Figure 11:
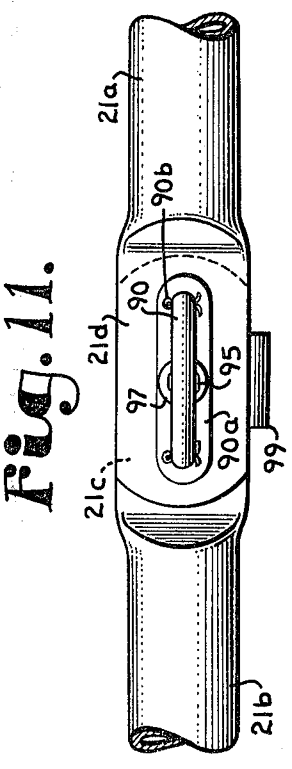

FIGS. 10, 11 and 12 are directed to the detail of the frame joint or connection immediately to the right of center in FIG. 1 which enables the translation from the horizontal frame construction to the elevated chair construction shown in FIG. 1 in full and dotted lines, respectively.

FIG. 10 is a top plan view of this joint with, in full lines, the joint shown locked in the horizontal position and, in dotted lines, the U shaped engaging bar being pulled out for translation of the joint from horizontal to upwards position. Reference is also made to the top right center of FIG. 3 where the opposed joint to this one is shown (in less detail) by the cutaway of a pad.

FIG. 11 is the joint of FIG. 10 in full lines seen looking from the bottom in FIG. 10 upwardly. This is a side view and an enlarged detail of the joint seen immediately right of center in full lines in FIG. 1.

Figure 18:
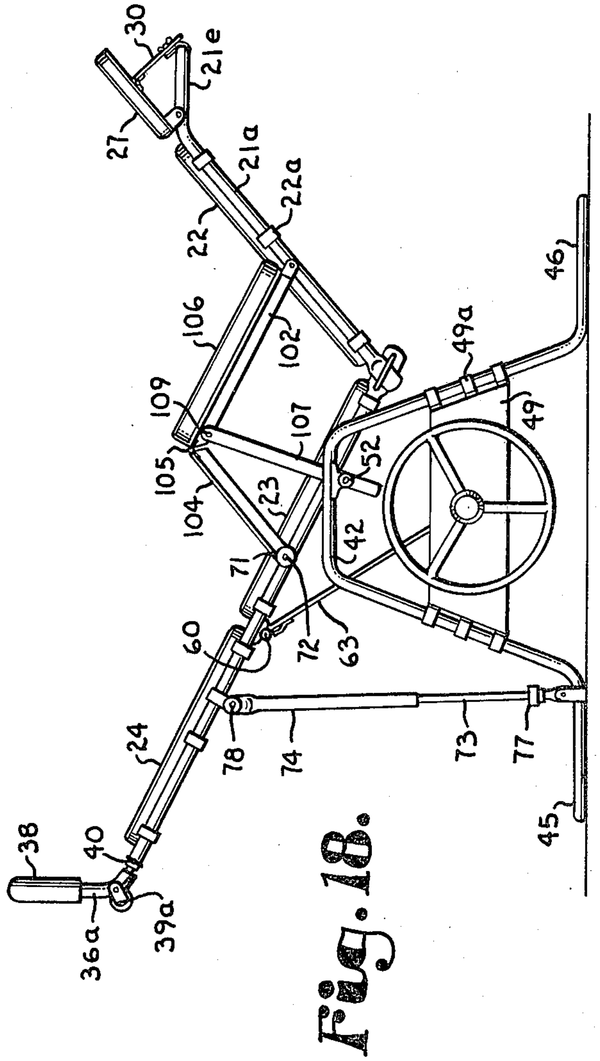

FIG. 12 shows the opposed joint to that of FIGS. 10 and 11 (the upper joint seen exposed in the top right center of FIG. 3) set and locked into the chair reclining position of the dotted lines of FIG. 1 and view of FIG. 18.

Figure 13:
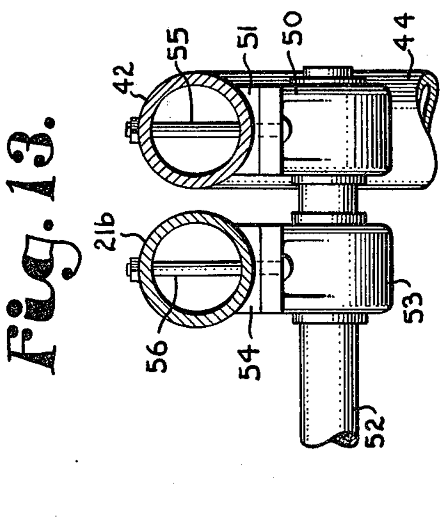

FIG. 13 is a view taken along the line 13—13 of FIG. 1 in the direction of the arrows.

Figure 3:
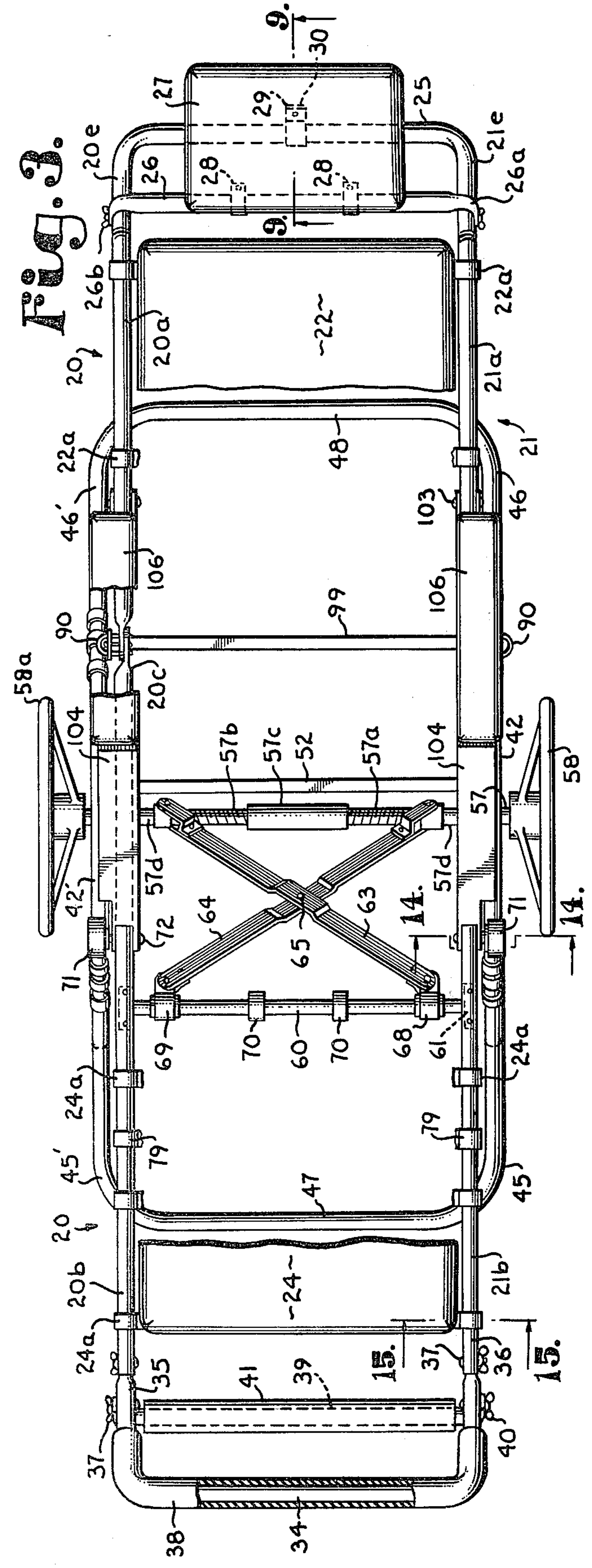
FIG. 3 is a vertical plan view, from above, of the full line showing (horizontal or level position of the body receiving frame) of the device of FIG. 1. In the view, parts and padding have been cut away to better illustrate the structure and relation of certain parts of the device.
Figure 14:
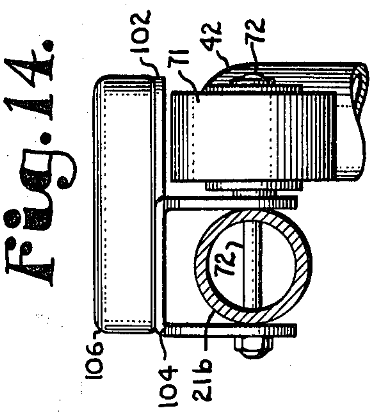

FIG. 14 is a view taken along the line 14—14 of FIG. 3 in this direction of the arrows.

Figure 15:
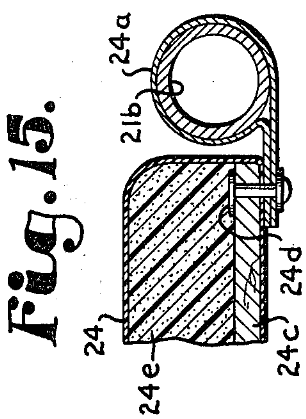

FIG. 15 is a view taken along the line 15—15 of FIG. 3 in the direction of the arrows.

Figure 16:
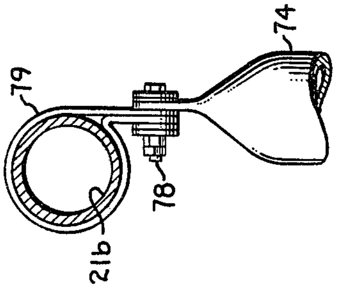

FIG. 16 is a view taken along the line 16—16 of FIG. 1 in the direction of the arrows.

Figure 17:
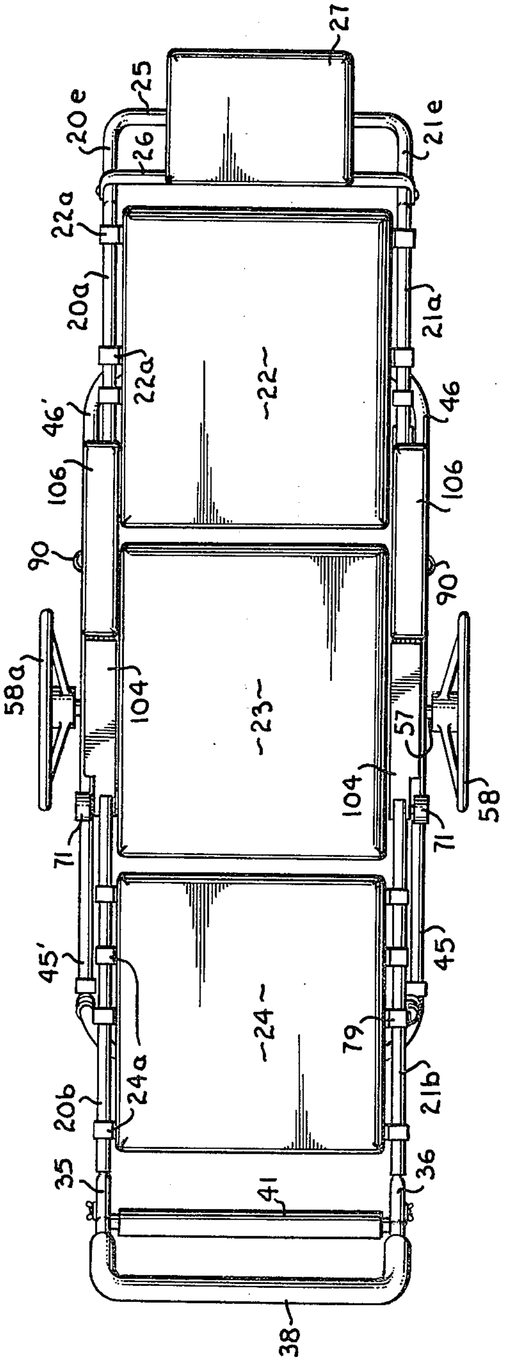

FIG. 17 is a top or vertical plan view from above, like that of FIG. 3, but showing the device without any cutting away, thus detailing the pads on which the individual using the device will lie or sit.

FIG. 18 is a side elevation of the device analogous to the dotted line showing of FIG. 1, but with the chair fully inclined.

Figure 19:
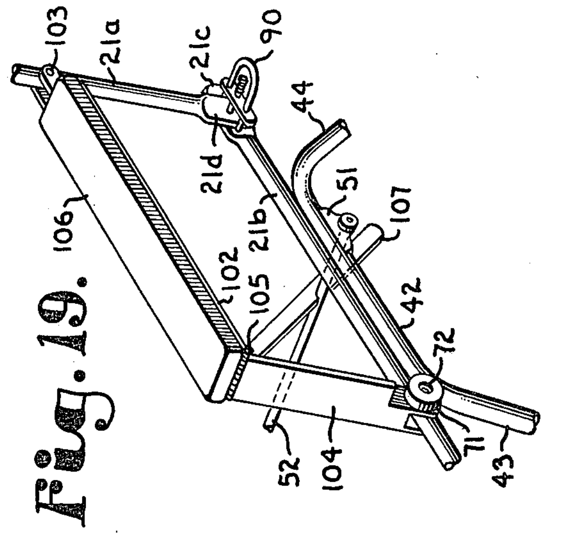

FIG. 19 is a three quarter perspective view from above and to the left in FIG. 1 showing the arm frame of the chair nearest to the viewer (as in the dotted line showing of FIG. 1 and full line showing in FIG. 17) in an erect position.

DESCRIPTION OF STRUCTURE

The subject device includes a base support, an elongate, normally flat frame pivotably mounted on the base support and means for tilting the frame with respect to the base support and then returning the frame to the normal horizontal position. Additionally, means are provided to transform the normally elongate flat frame into a substantially right angled chair construction. The specific structure of this device will be first described and, thereafter, its operation and function.

The elongate, normally horizontal frame is seen in side view in three positions in FIGS. 1, 2 and 18, the dotted line showing of FIG. 1 and the full line showing of FIG. 18 showing the frame in chair orientation. The frame is seen in plan view, vertical from above, in FIGS. 3 and 17. Referring particularly to, first, FIG. 3, in order to see both sides of the basic frame, a first elongate side member 20, generally designated, has a first, head end 20*a* and a second, longer, foot end 20*b*. The opposite elongate side member, generally designated 21, likewise has a relatively shorter head portion 21*a* and a relatively longer foot portion 21*b*. These elongate side frame members typically comprise elongate, parallel and normally horizontal, hollow metallic sleeves of aluminum, stainless steel or the like, of cylindrical form. The joined ends of members 20*a*–20*b*, 21*a*–21*b* are flattened for sliding abutment as at 20*c* and 20*d* (FIG. 12, also top right center of FIG. 3) and 21*c* and 21*d* (FIG. 10, as well as FIG. 11). The manner of interconnection of the frame sections with one another (elongate side members 20 and 21) so that the basic frame may be changed from the full line couch or bed form of FIG. 1 to the dotted line chair form thereof, as is illustrated in FIGS. 10–12, inclusive will be later described.

Now referring to FIG. 17 which is a vertical plan view similar to FIG. 3, but without the cutaways, there are preferably provided three padded rectangular rests 22 (head end), 23 (center of frame, but past the pivotal connection just described) and 24 (adjacent the foot end). Each of these pads (which have a strong, rigid structural base) are attached to the side frame members 20 and 21 by three sets of clips 22*a*, 23*a* and 24*a*, respectively. These clips or loops, which, inboard, are fastened to the underside of the bases supporting pads 22–24, inclusive, may be seen along the length of the side frame members 20 and 21 particularly in FIGS. 1, 3, 17 and 18. FIG. 15 shows a section through pad 24 with base 24*c*, fastener 24*d* and plastic foam filler 24*e*.

Referring to the head end, to the right in FIGS. 1, 3, 17 and 18, the side frame members are downwardly turned as at 20*e* and 21*e*, these members ending in transverse, normally horizontal beam 25. As may be seen in FIG. 2, when the frame is fully tilted from the horizontal position with the head end down and the foot end up, the cross beam 25 will normally rest on a normally horizontal floor or surface. The downward angle of end portions 20*e* and 21*e* is approximately 45 degrees from the line of the side member.

Without limitation, but in order to give an idea of the typical scale involved, the length of the entire frame assemblage from padded transverse member 34 (to be described) to the head end edge of head pad 27 (to be described) is approximately 7 feet. The width between centers of side frame members 20 and 21 is typically approximately 21 inches and the height of the frame side members 20 and 21 from a horizontal floor surface when the frame is in horizontal position, as in full lines of FIG. 1, is approximately 21 inches. Within such scale the pads 22–24, inclusive illustrated are typically 19 inches long by 18 inches wide. The straight line length of the head end of the frame (members 20*a* and 21*a*) from the center of the pivot to beam 25, is preferably approximately 28 inches. When a six foot man is lying on the horizontal frame with his feet engaged with the foot end in the manner to be described, the top of his head will be approximately two inches short of the right hand end of pad 22 in the views of FIGS. 1 and 3. Accordingly, the head pad to be described is used in the horizontal position only by extremely tall individuals, if at all and is designed for use in the chair position of the dotted lines of FIG. 1 and full lines of FIG. 18. The adjustability for length of the foot end of the frame to greater than that shown also makes this the case.

Referring, then, to FIG. 9, which is an enlarged detail of the extreme head end of the frame, and the right hand ends of FIGS. 1, 2, 3, 17 and 18, transverse cylindrical beam 26 is provided, fastened at its ends to side member portions 20e and 21e. Head pad 27 has a rigid, rectangular base structure 27a. Beam 26 overlies side member portions 20e and 21e and has downwardly turned ends 26a that overlie the outboard sides of member portions 20e and 21e. A pivotal attachment which permits some inward and outward adjustment of transverse bar or member 26 over its pivotal attachment, by wing nuts 26b, is provided. A pair of spaced apart brackets 28 encircle member 26 and are fixed to the inboard underside of frame 27a, thus pivotally mounting the inboard end of pad 27 with respect to beam 26. A hinge member 29 is fixed outboard of the underside of frame 27a, centrally thereof, having elongate strap 30 fixed to one side of the hinge. Strap 30 has holes or openings 31 therein adjacent the depending lower end thereof. A loop bracket 32 encircles end cross beam 25 centrally thereof and is removably and adjustably engageable by bolt 33 (having a wing nut on the threaded end thereof) which engages an opening in bracket 32 and one opening in strap 30. Shortening or lengthening the engaged portion or strap 30 adjusts the angle of the position of pad 27 with respect to its pivotal mounting on beam 26.

Turning to the foot extreme end of the frame, there is a U-shape end beam is provided which has transverse end portion 34 making up the base of the U and inboard leg portions 35 and 36, which portions telescope into the hollow ends of side members 20b and 21b. A plurality of openings are provided along the end lengths of U legs 35 and 36 which are adjustably engagable by bolts 37 having wing nuts on the free threaded ends thereof. This adjustment at the foot end enables the extension of the foot frame for relatively tall or taller individuals so that their heads will be fully received on pad 22 when lying in the supine position with their feet engaged with the foot frame end members (as will be described). A resilient foam rubber or compressible plastic sleeve 38 overlies the entire U base beam member 34 and the upwardly angled portions 35a and 36a of the U member legs at the foot end. The upward angling of the foot end members is preferably greater than the downward angling of head end portions 20e and 21e, in the range of from 45 to 60 degrees.

A transverse heel engaging beam 39 is provided, substantially at the base of the upwardly angled portions 35a and 36a. Beam 39 preferably has right angle tab members 39a at the ends thereof which are pivotally fixed to U legs 35 and 36 by bolts 40 having wing nuts on the threaded ends thereof. A rubber or plastic resilient sleeve 41 overlies member or beam 39 in the substantial length thereof.

The upward angling at 35a and 36a of the foot end of the frame, as well as the provision of beam 39 and the cushioning of beams 34 and 39, including U legs 35a and 36a, is to enable the supine user of the device to insert his feet between beams 34 and 39, with the toes of the user's feet hooked outboard of leg portions 35a and 36a against foam padding 38. Additionally, the user's heels are hooked outboard past beam 39 against the rubber or foam padding 41 with the ankles of the user's feet (and Achille's tendons of the user's ankles) overlying the padding 41 on beam 39. Yet further, preferably, the user's feet are pushed to the extreme left and right, respectively, to ensure that the upper portion of the user's arches also abut against the padding sleeve 38 at the corners, in order to give more suspension support. The in and out length adjustability of the U foot end member and the pivotal adjustment of beam 39 around bolts 40 enable adjustment to any size foot of a mature, grown, adult user.

Turning to the supports for the described basic frame, the base of the device essentially comprises a pair of A-frame members which are parallel oriented and adapted to rest on a floor or ground surface with the lower ends of the legs of the A's. In the drawings, the flat, horizontal tops of the A-members are designated 42 and 42′, respectively, the side legs of the A-members being designated 43 and 44 (43′ and 44′) and the foot or lower end members of the A-supports numbered 45 and 46 (45′ and 46′). The lower, floor contacting A-support legs are connected at their outboard ends by transverse portions 47 and 48 (FIG. 3), thus giving a rigid, stable support with the normally horizontal frame previously described, when the connecting shafts to be described are also considered.

Mounted between and rigidly strapped or connected to the downwardly extending A-support frame members 43 and 44 (43′ and 44′) are rigid metallic plates 49 (FIGS. 1 and 18) having securing strap members 49a effecting rigid connection of plates 49 with the leg members 43 and 44 (43′ and 44′) and, additionally, carrying an operating shaft therebetween to be described.

A first pair of pillow blocks 5 are fixed by suitable conventional bracket means 51 to each underside of tops 42 and 42′ of the A-frames, displaced toward the head end off center as seen in FIGS. 1 and 18. A first cylindrical shaft 52 is rigidly received and fixed in said pillow blocks 50, therebetween. (Reference is here made to FIG. 13 showing a section through the A-frame apex looking to the right in the view of FIG. 1.) A second pair of bearing collars 53 are each fixed to one underside of the elongate sleeve members 21b and 20b, respectively, intermediate the ends thereof, by conventional bracket means 54, such axially in line with pillow blocks 50. Bolts 55 hold brackets 51 on the A-frame apex members 42, 42′, while bolts 56 hold brackets 54 on side member portions 21b and 20b. The first pair of pillar blocks 50 are the first bearing collars, while the second air of bearing collars 53 are the second bearing collars.

As clearly may be seen in the views of FIGS. 1 and 3, shaft 52 and blocks 50 carrying it are mounted on the foot end of the frame past the pivotal engagement of side frame member portions 20a, 20b and 21a, 21b, although toward the head end off center on the A-frame apex members 42, 42′. The mounting of shaft 52 in bearing collars 53 is pivotal (not fixed as shaft 52 is in pillow blocks 50) so that the frame (seen horizontal in the full lines of FIGS. 1 and 3) may pivot on shaft 52 to the positions seen in FIGS. 2 and 18 or intermediate angles with respect thereto as will be described. The capacity of the said frame to pivot with respect to the A-frame bases is controlled and effected in a manner to be described herebelow in detail.

A second cylindrical shaft generally designated 57 is rotatably received through openings 49b in plates 49 which carry suitable bearing members 59 (FIG. 4) fixed therein which rotatably receive said shaft 57. Fixed to the outer ends of shaft 57 (outboard of plates 49 and the bearings carried thereby) are two wheels 58 and 58a. Rotation of shaft 57 in clockwise direction in the view of FIG. 1 (full lines) is effected by rotation of wheels 58 and 58*a,* in such direction. From the angled position of FIGS. 2 and 18, counterclockwise rotation of shaft 57 is effected by counterclockwise rotation of wheels 58 and 58*a.*

Yet a third preferably cylindrical shaft 60 is rigidly received in bearing or pillow blocks 61 fixed to the undersides of side members 21*b* and 20*b* toward the foot end of the frame and outside the A-frame base members. As may be seen in the figures, the basic shaft 52 mounting the normally horizontal frame on the A-frame base members is fixed near the right hand end of the foot portion of the base frame as seen in the views and somewhat to right of center on the A-frame base member apexes. Drive shaft 57 for tilting and returning the frame (as will be described in detail), FIGS. 1 and 4, is centrally mounted of the A-frame bases and centrally of plates 49, slightly to the left of shaft 52 in the views. Shaft 60, which is rigidly mounted with respect to the side frame members 21*b* and 20*b* is positioned substantially to the left (toward the foot end) on the foot end frame member portions 21*b* and 20*b* with respect to shaft 52.

Turning, now, to the drive means for tilting and returning the frame from the horizontal position of the full line (for supine use) showing of FIG. 1 to the tilted position of FIGS. 2 and 18, shaft 57 has oppositely threaded portions 57*a* and 57*b* thereon intermediate the ends thereof, same spaced apart from one another centrally. Centrally mounted of shaft 57, inwardly bounding the oppositely threaded portions 57*a* and 57*b* is stop 57*c*. Outboard stops 57*d* on shaft 57 bound the outboard limits of oppositely threaded screw portions 57*a* and 57*b*.

Referring particularly to FIGS. 3–8, inclusive, an X frame generally designated 62, made up of two centrally pivoted arms 63 and 64, communicates between and is connected at the lower ends 63*a* and 64*a* to second shaft 57 and at the upper ends (63*b* and 64*b*) with third shaft 60. The pivotal connection is at 65, centrally of the arm member 63 and 64, which central portions are offset as seen in FIG. 6 for aligned outer arm portions. The mentioned shaft connections are seen in FIG. 7 (shaft 60) and FIG. 8 (shaft 57).

Specifically, the lower ends 63*a* and 64*a* of the X frame arm members are bifurcated to engage internally threaded nuts 66 and 67 which threadably engage the shaft 57 threaded portions 57*a* and 57*b,* respectively. The connections are pivotally by pins so arm members 63 and 64 may change angular position with respect to nuts 66 and 67. Upper ends 63*b* and 64*b* are also bifurcated as may be seen in FIG. 7 for pivotal engagement to linear bearings 68 and 69 via tabs 68*a* and 69*a* depending therefrom. Stops 70 (paired or single) may be provided centrally of shaft 60 to provide a cooperating stop means to limit elongation of the X frame by motion of the ends thereof together, as may be seen in FIG. 5.

FIG. 4 shows the X frame reduced in length by motion a part of the ends thereof. As will be described, the movement together of nuts 66 and 67 on threaded portions 57*a* and 57*b* of shaft 57 by rotation of handwheels 58 and 58*a* lengthens the X frame along the longitudinal axis of the main frame, thus lifting the foot end of the frame as seen in the views of FIGS. 2 and 18. The opposite action, resulting in the shortening of the X frame along the axis of the main frame (20, 21), as seen in FIGS. 3 and 4, operates to return or maintain the position of the foot end of the frame at horizontal as seen in FIGS. 1, 3 and 17. The stops 57*d* aid in limiting the counterclockwise movement of the frame in the views of FIGS. 1, 2 and 18 by limiting the shortening of the X frame, the latter particularly seen in FIGS. 3 and 4. If stops 57*d* are not present, thread action can continue past head beam 25 contact with floor horizontal.

Additional means are provided to control and limit the movement of the end ends of the frame around shaft 52 in the counterclockwise direction in FIGS. 1, 2 and 18. The first of these comprises cylindrical rubber or plastic stops or buffers 71 which are mounted on ends of shafts 72 (FIG. 14) which are carried through frame member portions 21*d* and 20*b*. Stops 71 abut the end edges of the A frame apexes 42, 42′ as particularly seen in FIGS. 1, 3 and 14 when the foot end of the frame comes down into horizontal position.

The second limits comprise two sets of telescoping beams 73 and 74, the former slidably received within the other, There is a pair of opposed sets of telescoping shaft members, one on each side of the frame, each set connecting between the base of an A frame member at the foot end of the frame and the elongate side member on that frame end on one side of the frame. Shafts 73 are pivotally (75) strapped (76) to the base leg portions 45, 45′ at the inboard ends thereof. Shafts 73 carry stops 77 fixed thereon adjacent the lower ends thereof. Sleeves 74 are pivotally mounted as at 78 on straps 79 fixed to side frame members 21*b* and 20*b* outboard of shaft 60. The functions of shafts and sleeves 73 and 74 are two fold. First, they cooperate with the basic frame (20, 21) mounting on shaft 52 to stabilize the tracking of the frame with respect to the A frame base members in actual pivotal action. Secondly, as the foot end of the frame reaches the horizontal position of FIG. 1, the nuts 66 and 67 bear on stops 57*d,* stops 71 bear on frames 42, 42′ and, should excessive weight be placed on the foot end of the frame outboard of shaft 52 and stops 71, sleeves 74 will bottom on stops 77.

FIGS. 10–12, inclusive show the nature of the disengageable locking means which secures the frame in either horizontal position (or entirely level position), as in FIGS. 10 and 11, and chair or seated mode or substantial right angle position, as in FIG. 12. Referring, then, particularly to these figures, a pair of U-bolts 90 are employed on each side of the frame, at the juncture of the head and foot ends thereof, to alternately engage only openings 91 in head frame end portions 20*d* and 21*d* as in FIG. 12 over upper and lower edges of foot frame end members 20*c* and 21*c* or, alternatively, the said openings 91 and openings 92 in foot frame end portions 20*c* and 21*c,* when openings 91 and 92 are aligned with one another as in FIGS. 10 and 11.

Said otherwise, to lock together the frame part end portions 20*c* and 20*d* on one side and 21*c* and 21*d* on the other side in such position that the head and foot frame members are axially aligned with one another, the said end portions 20*c* and 20*d* (and 21*c* and 21*d*) are overlapped, one with the other, as in FIGS. 10 and 11, so that openings 91 and 92 are in registry with one another. The legs of U bolts 90 then engage therethrough. Alternatively, by disengaging the U bolts with such registered openings 91 and 92 on each side of the frame, the head frame members 20*a* and 21*a* may be raised to substantial right angles so that openings 91 are clear of portions 20*c* and 21*c,* thus permitting the engagement of U bolts 90 with openings 91 above and below the upper and lower edges of the foot frame member end portions 20*c* and 21*c*. When head end frame members 20*a* and 21*a* are rotated back from vertical slightly clockwise as in FIG. 12, the ends of bolt 90 register against the top and bottom edges of frame member portions 20*c* and 21*c* and thus lock the members against further movement with respect to one another until the U bolts are disengaged. There is the arcuate pivot over 90 degrees which may be employed to disengage the U bolts for return to the axially aligned or horizontal position, but, when a user is sitting on the pad 23, leaning back against the pad 22, the end portions will be in the relationship seen in FIG. 12.

There is provided a spring loaded mount for the U bolts 90 on each side of the frame. In each case (particularly see FIG. 10), this comprises an elongate bolt 93, threaded, which carries thereon nuts 94 and 95. Two washers 96 and 97 carry therebeween spring 98. The U bolts 90 each carry a plate 90*a* removably mounted thereon by pins 90*b* removably engaging openings through the legs of the U bolt. Spring 98 abuts between plate 90*a* and washer 97 to provide the spring loading for the action of the U bolts, maintaining them in locked in openings 91 (FIG. 12 or 91 and 92 (FIGS. 10 and 11), once set therein.

A strap 99 is preferably provided extending between the end portions 20*c* and 21*c*, which are the inboard portions of the foot frame member ends. This serves to brace the ends apart in fixed relationship at the critical chair base juncture and also permits the employment of a seat pad 23 support centrally of the underside thereof (not seen) overlying strap 99. Other washers 100 and 101, fixed respectively to the bolt head and nut 94, serve to slidingly space flat portions 20*c* and 20*d* and 21*c* and 21*d* with respect to one another.

An arm rest configuration is additionally provided on each side of the body frame. Particularly referring to FIG. 19, FIG. 18 and the dotted line showing of FIG. 16, a first beam or member 102 is pivotally mounted at one end by pin 103 intermediate the length of side frame members 20*a* and 21*a*. A second beam or member 104 is pivotally mounted at one end at shaft 72 on foot frame members 20*b* and 21*b* past shaft 52. Beams 102 and 104 are hingedly mounted at the other ends thereof to one another at 105. A pad 106 is fixed to the top of beam 102 and extends substantially the length thereof. Lock beams 107 having slots 108 intermediate the ends thereof are pivotally mounted at 109 on the underside of beams 102. Beams 107 are engageable and disengageable with shaft 52 to provide an additional support and lock for the chair position, in addition to the U bolts 90. Just as the head frame members 20 and 21*a* are moved up to substantial right angles to enable the U bolt engagement in openings 91 for return to the less than 90 degree angle of FIG. 12, the initial right angle positioning of the head frame member end with respect to the foot frame member end enables the beams members 107 to be laid against shaft 52 for slot engagement therewith as seen in FIG. 19 when the position of FIG. 12 is assumed. A horizontal tie may connect the lower ends of members 107 so they move in conjunction with one another (not shown).

OPERATION IN THE SUPINE POSITION

Before the user lies down (face up) on the couch or bed, the device must first be in a fully horizontal position, with the two U bolt locks (FIGS. 10–12, inclusive) fully inserted as in FIGS. 10 and 11. These locks hold the head end of the bed in a rigid, straight position. To obtain the horizontal, bed like position, wheels 58 and 58*a* are turned counterclockwise in FIG. 1 (toward the foot end) as far as they will readily go.

The user sits, facing outwardly, on the center pad 23 of the couch with the feet on or hanging toward the floor over either hand wheel. Next, the user's feet are swung up and onto the leg pad 24 of the bed, still in the sitting position.

The user then inserts the feet in between the upper and lower cushioned cross members 34 and 39 to obtain a foot hold. The user's heels are hooked over the lower padded member 39 with the toes positioned behind the upper padded cross member 34. The user then spreads the feet as far apart as possible until the toes are under the curved end 35*a*, 36*a* of the upper padded cross member. With the user's hands, the body is pushed sufficiently back toward the head end to tighten the heel and toe hold.

The user starts tilting the device by pulling backwardly (toward the head end, clockwise in FIG. 1) on wheels 58, 58*a* from the top rim of each hand wheel. The user may stop at any incline angle desired. The tilt will hold automatically at any angle. Alternatively, the user may continue the tilt by rotation of the wheels until the head frame beam 25 reaches the floor. Resistance to the hand wheel pull (abutment against stops 57*c* and 70) signals when to stop rotating the wheel. At this position, the frame is tilted at the maximum angle, about 30 degrees, typically 25 to 26 degrees.

The user may stay in an inclined position, relaxing and resting, for a preferred interval, typically no longer than about five minutes at a time in initial use. The user rests the hands on the stomach or top of the hand wheels when the frame is in tilted position. The user does not put the hands under the frame at any time. If, in the full tilt position, the user's heels are loosened and/or the user's feet disengage, one does not try to elevate the bed back to horizontal. Once body balance on the couch is broken, the bed (and body) cannot readily be elevated back to horizontal. In such case, the user eases the body back, down and completely off the head end of the bed onto the floor. Upon rising, the user returns the bed to the horizontal position by wheel rotation and starts over again. Disengagement does not happen if firm heel and toe locks are made at the beginning and tilt angle is gradually experienced and become accustomed to.

To return to the full horizontal position, the user pushes the hand wheels forward in rotation (toward the foot end of the frame or counterclockwise in FIG. 1) as far as they easily go (abutment against stops 57*d*, also stops 71 and possibly stops 77). At this point the frame is in full horizontal position. The user then disengages the feet and lies on the bed frame a minute or two, relaxing. Then, with each hand extended forwardly, the user holds onto a side of a frame with each hand and, with pressure on the elbows, raises the body to a sitting position. The user then swings the legs off the bed, placing the feed on the floor, remaining seated on center pad 23.

In the case of any substantial serious or medical impairment, or illness, the user should consult a physician before any use of the device.

USE IN CHAIR POSITION

With the frame initially in the full horizontal position of the full lines of FIG. 1, the user first releases the two U bolts, one on each side of the frame, by pulling them outwardly (dotted lines of FIG. 10). The head end of the frame may be worked by raising and lowering it slightly to make this easier. Each U bolt is turned slightly, after being pulled out, so that they will not pop into the locking openings.

Next, the user, with one hand, reaches to the head end of the bed and raises the frame end upwardly around the pivot (FIG. 12) until the head end of the frame is substantially at right angles to the foot end thereof and so that the two openings in portions 20*d* and 21*d* are fully exposed. At this point, the operator reengages the U bolt members on each side of portions 20*c* and 21*c* in the hole openings of parts 20*d* and 21*d* by pushing inwardly on the U bolt members until each locks over the upper and edges of portions 20*c* and 21*c*. The two pivotal slotted bar members (one hanging from each arm rest underside) are manipulated to make sure that each is snapped over the shaft 52 in the slot thereon. The user is not to sit in the chair until certain that all four engagements, two on each side, are positively made. At this point the lounge chair is ready to be sat upon. A beam, not shown, may interconnect the slotted bar members so they may be engaged and disengaged simultaneously with shaft 52.

The user sits between the arm rests on pad 23, pushing the body all the way back on the seat against pad 22. The user then extends the legs forwardly toward the foot end of the frame but does not engage heels and toes between the end frame members in foot hold. This is not necessary in the body seated position and also not feasible for any but the largest size users with the body properly oriented on the seat and chair.

To start tilt, again, the operator or user rotates wheels 58, 58*a* in the clockwise direction of FIG. 1, that is, backwardly from the tops of the rims of the hand wheels toward the head of the frame. The frame tilts or returns to the horizontal position in the same direction that the user's hands impel the hand wheels. The tilt may be stopped at any angle and the frame automatically holds at that angle.

The tilted, seated reclining position is for rest and relaxation and, for example, are particularly restful for those who must stand or drive a car for long periods of time, as well as those bothered with varicose veins. The user may stay in the seated, reclining position at any angle for as long or often as desired. The frame is then returned to the horizontal position by reverse movement of the hand wheels. The user is not to get on or off the frame or bed in either chair or couch orientation while such is in any tilted position.

To convert from the chair orientation or seated position to horizontal bed or couch position, the U bolt members are again disengaged from the openings in members 20*b* and 21*b*. This is best accomplished by rotating members 20*a* and 21*a* in the counterclockwise direction in FIG. 12 to completely free the U bolt members from engagement with the top and bottom edges of members 20 and 21*c*. The N member are held back, disengaged, while the head end of the frame is pushed downwardly to the full horizontal position and the openings again are aligned with one another. At this point, the U bolt members are reengaged through the openings in members 20*d* and 21*d* and 20*c* and 21*c* as seen in full lines in FIGS. 10 and 11.

It is well for the user or operator to test the tilting action of the frame and its return before getting on it and using it each time in either horizontal or chair use position. Specifically, the user may move the frame to full tilt and return it to the horizontal position, in order to see that it is in perfect working order and that the stops are operative before use. Additionally, the positive engagement of the U bolts members in either the positions of FIGS. 10 and 11 (horizontal) or 12 (chair position or right angles) and the depending beam engagement in the latter should be checked before each use.

While generally and most often the device is employed with the user face up (back down) in supine position, certain effects and results may call for a face down or side down reclined position. In all such cases suitable supervision and/or angular control and/or additional (strap for example) securements may be helpful. In resting in the frame horizontal position the user may be face down, on his back or on one side.

From the foregoing, it will be seen that this invention is one well adapted to attain all of the ends and objects hereinabove set forth together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

I claim:

1. A therapy device comprising, in combination:

a pair of parallel oriented A-frame base members adapted to rest on a ground or floor surface with the lower end of the legs of the A, a pair of first bearing collars, one fixed to each underside of the tops of the A-frames, a first transverse cylindrical shaft received in and carried by said first bearing collars, an elongate, rectangular, body-receiving frame having elongate side members and shorter transverse head and foot end beam members, the said body-receiving frame configured at the ends thereof so as to provide a downwardly angled head end and an upwardly angled foot end, a pair of second bearing collars, one fixed to each underside of the elongate side members of the body-receiving frame intermediate the length thereof, said second collars engaging and carried by the first cylindrical shaft inboard of the first bearing collars whereby said frame is positioned inboard of the A-frame members, the frame pivotable with respect to the base members on its first shaft mounting, two opposed, substantially parallel plate members, one carried between each pair of A-frame legs and fixed thereto, a second transverse shaft rotatably received between said two plate members below said first shaft and extending through said plate members at the ends thereof, a turning wheel removably fixed to at least one end of the second shaft outside of the said plate members, a third transverse shaft mounted on said extending between the elongate frame side members and located between the first shaft and the foot end of the frame, the second shaft having opposed, reversed screw threads thereon intermediate the outboard ends thereof and inboard of the plate members, the said reversed threads spaced centrally apart from one another on the second shaft, an X frame made up of two centrally pivoted elongate arm members communicating between and connected at the ends of the members thereof to the said second and third shafts, the lower connection being by nuts pivotably mounted on the lower ends of the X frame members which are threadably engaging the said second shaft screw threads and the upper connection being by bushings pivotably mounted on the upper ends of the X frame members which are slidably engaging the third shaft, whereby rotation of the second shaft in one direction moves the nuts engaging the second shaft screw threads toward one another, thus lengthening the X frame along the longitudinal axis of the frame and elevating the foot end of the frame from normal horizontal upwardly, and rotation of the second shaft in the other direction moves the nuts engaging the threads away from one another, shortens said X frame along said axis, thus lowering the foot end of the frame toward normal horizontal, the upwardly angled foot end of the body receiving frame having a transverse beam member extending between and connecting the said elongate side members adjacent the ends of the straight portions thereof and the upwardly angled foot end, and a plurality of body carrying, transverse support members provided communicating between and carried by the elongate side members along the length thereof between the downwardly angled frame head end and upwardly angled foot end.

2. A device as in claim 1 including means for limiting the upward movement of the foot end of the frame comprising means for limiting inward movement of the X frame lower connection nuts threadably engaging the second shaft towards one another, said last means specifically comprising a stop positioned centrally of said second shaft against which said nuts abut as the upward inclination of the foot end of the frame approaches its permitted extreme.

3. A device as in claim 1 including means on said third shaft for limiting the inward travel of said X frame upper connection bushings toward one another, said means comprising at least one stop fixed to said third shaft between said bushings, thereby to aid in limiting the upward inclination of the foot end of the frame at its permitted extreme.

4. A device as in claim 1 wherein the elongate side members of the body receiving frame are each divided and pivotably hinged between the first cylindrical shaft and the head end of frame, whereby the substantial length of the head end of the frame may be pivoted upwardly from level, normally horizontal, couch configuration to substantial right angles with the center portion and foot end of the frame, thereby to form a chair configuration, an arm rest on each side of the body-receiving frame, each rest comprising a first piece pivotally mounted at one end thereof to the elongate side member past the hinge towards the head end of the frame and a second piece pivotally mounted to the elongate side member past the hinge towards the foot of the frame, these first and second two pieces pivotally joined at their free ends, thereby forming a substantially right angled arm receiving shelf when the frame is in chair configuration and means for alternatively and fixedly locking the frame in the couch and chair configurations, respectively, comprising: (a) third pieces each pivotally connected at one end to the free end connections of one set of the first and second pieces and having a portion of the length thereof arcuately relieved to be able to overlie and engage the first cylindrical shaft and (b) pivotal locking means adapted to alternatively and removably engage and lock together the hinge ends of the frame side members in a first, in line, relationship for the straight line frame couch configuration and a second, sharply angled, relationship for the substantial right angle frame chair configuration, said locking means including a horseshoe member resiliently yet fixably mounted with respect to the divided and pivotally hinged connection of each side of the side frame members with one another, said horseshoe members each removably yet fixably engageable through both divided portions of one frame side member in horizontal couch orientation thereof and alternatively engageable through one of said divided portions and around the other said divided portion in right angle chair orientation thereof.

5. A device as in claim 1 including an inboard transverse beam member extending between and connecting the elongate side members adjacent the ends of the straight portions thereof at the downwardly angled frame head end, there being a head end transverse end member as a part of said rectangular body receiving frame, a head receiving pad mounted on said head end transverse beam member and the head end transverse end member, said head receiving pad being pivotably mounted at one end thereof on said head end inboard beam member and arcuately adjustably connected to the head end transverse end member, whereby to permit angular adjustment of said head receiving pad with respect to said frame.

6. A device as in claim 1 including means for limiting downward angular movement of the foot end of said frame at a substantially horizontal position thereof, whereby the foot end of the frame may only be angled upwardly and returned to said horizontal position, said latter means including buffers on the side members of said frame positioned substantially centrally thereof, but toward the foot end of the frame from said first transverse shaft, said buffers positioned outboard of the frame elongate side members and adapted to contact upper portions of the A-frame members as the body receiving frame foot end reaches substantially horizontal position.

7. A device as in claim 1 including means for limiting downward angular movement of the foot end of said frame at a substantially horizontal position thereof, whereby the foot end of the frame may only be angled upwardly and returned to said horizontal position, said last means including collar means positioned peripherally adjacent the ends of the second shaft, said last means limiting the outward movement of the X frame lower connection nuts away from one another on the screw threads, thus to limit the lateral expansion of said X frame.

8. A device as in claim 7, wherein said last means also includes buffers on the side members of said frame positioned substantially centrally thereof, but toward the foot end of said frame from said transverse shaft, said buffers positioned outboard of the frame elongate side members and adapted to contact upper portions of the A frame members as the body receiving frame foot end reaches substantial horizontal position.

9. A device as in claim 7 wherein said last mentioned means also includes a pair of opposed sets of telescoping shaft members, one member of each set received within the other, said sets each connecting between one side of the base of the A frame members next to the foot end of the frame and one of the elongate side members adjacent the front end of the frame, one set on each side of the frame, there being provided stops limiting the telescoping engagements of said sets of shafts, one with the other, as the foot end of the frame approaches substantial horizontal position.

10. A device as in claim 1 including means for limiting downward angular movement at the foot end of said frame at a substantially horizontal position thereof, whereby the foot end of the frame may only be angled upwardly and returned to said horizontal position, said latter means including a pair of opposed sets of telescoping shaft members, one member of each set received within the other, said sets each connecting between one side of the base of the A-frame members next to the foot end of the frame and one of the elongate side members adjacent the foot end of the frame, one set on each side of the frame, there being provided stops limiting the telescoping engagements of said such of shafts, one with the other, as the foot end of the frame approaches substantial horizontal position.

11. A device as in claim 10 wherein said last mentioned means also includes buffers on the side members of said frame positioned substantially centrally thereof, but towards the foot end of said frame from said transverse shaft, said buffers positioned outboard of the frame elongate side members and adapted to contact upper portions of the A-frame members as the body receiving frame foot end reaches substantial horizontal position.

12. A device as in claim 11 wherein said last mentioned means further includes collar means positioned peripherally adjacent the ends of the second shaft, said collar means limiting the outward movement of the X-frame lower connection nuts away from one another on the screw threads, thus to limit the lateral expansion of said X-frame.

13. A device as in claim 1 including means for limiting the upward movement of the foot end of the frame comprising:

(a) means for limiting inward movement of the X-frame lower connection nuts threadably engaging the second shaft towards one another, said last means specifically comprising a stop positioned centrally of said second shaft against which said nuts abut as the upward inclination of the foot end of the frame approaches its permitted extreme; and (b) means on said third shaft for limiting the inward travel of said X-frame upper connection bushings towards one another, said means comprising at least one stop fixed to said third shaft between said bushings, therby to aid in limiting the upward inclination of the foot end of the frame at its permitted extreme.

* * * * *